United States Patent [19]
Landis et al.

[11] Patent Number: 5,588,836
[45] Date of Patent: Dec. 31, 1996

[54] MOUTH PROP AND TONGUE DEFLECTOR APPARATUS

[75] Inventors: Timothy J. Landis, Loomis; Scott M. Perry, Auburn, both of Calif.

[73] Assignee: OP-D-OP, Inc., Roseville, Calif.

[21] Appl. No.: 543,843

[22] Filed: Oct. 23, 1995

[51] Int. Cl.$^6$ .......................... A61C 17/06; A61C 17/14
[52] U.S. Cl. .............................................. 433/93; 433/94
[58] Field of Search .................................. 433/91, 93, 94, 433/96, 136, 140

[56] References Cited

U.S. PATENT DOCUMENTS

| | | | |
|---|---|---|---|
| 674,650 | 5/1901 | Lundborg | 433/93 |
| 2,102,263 | 12/1937 | Grunewald | 433/94 |

FOREIGN PATENT DOCUMENTS

132142  11/1945  Sweden ..................... 433/94

*Primary Examiner*—Nicholas D. Lucchesi
*Attorney, Agent, or Firm*—John P. O'Banion

[57] ABSTRACT

A mouth prop and tongue retractor apparatus for use in dental procedures. The apparatus includes a handle rotatably mounted within a base. A ball joint on the base fits within a socket in a mouth prop to provide pivotal positional adjustment of the apparatus. An elongated aspirator tube extends through the handle and base, and is coupled to a tongue retractor. A suction aperture on the tongue retractor communicates with the aspirator tube and provides for saliva removal from a patient's mouth. Rotation of the handle provides extension adjustment for the aspirator tube and tongue retractor.

20 Claims, 7 Drawing Sheets

MOUTH PROP AND TONGUE DEFLECTOR APPARATUS

BACKGROUND OF THE INVENTION

1. Field of the Invention

This invention pertains generally to dental mouth props and suction devices, and more particularly to a mouth prop and tongue retractor apparatus which holds a dental patient's mouth open, adjustably positions a patient's tongue, and evacuates saliva from a patient's mouth during dental procedures.

2. Description of the Background Art

Dental props, tongue positioners, and saliva evacuation devices are commonly used in dental and oral surgery practice. Such devices facilitate dental and oral surgery procedures by improving visibility and increasing the available working space within a patient's mouth, and by removing saliva from the patient's mouth which would otherwise accumulate and interfere with dental operations and generally increase patient discomfort. Saliva removal is further necessitated because dental procedures frequently involve substances, such as mercury amalgam particles, which are unhealthy to ingest and would otherwise be swallowed by a patient if not removed by suction.

Several devices are known in the dental and oral surgery professions for positioning a patient's mouth and tongue during treatment and/or removing saliva and debris therefrom. For example, U.S. Pat. No. 5,232,362 discloses a dental suction appliance wherein a tongue deflector is coupled to an aspiration tube and held in place by a bite tube between a patient's teeth. U.S. Pat. No. 5,125,686 discloses a dental appliance which includes a tongue stabilizer and suction tube that are slidably coupled to a bite block. U.S. Pat. No. 4,975,057 discloses a dental appliance in which a bite block includes apertures which serve as evacuation nozzles. U.S. Pat. No. 4,281,986 discloses a dental appliance wherein a collector member having a tongue guard and collector membrane is held in place by a bite block. U.S. Pat. No. 4,192,071 discloses a dental appliance having a collector member with a tongue guard and collector membrane held in place by a bite block. U.S. Pat. No. 4,167,814 discloses a mouth prop and oral evacuation device wherein a generally U-shaped suction tube and tongue guard are secured to a mouth prop. U.S. Pat. No. 4,024,642 discloses a dental appliance having a suction tube and flat shield which are attached to a bite block. U.S. Pat. No. 3,924,333 discloses a dental appliance in which a tongue guard member with a series of evacuation channels is connected to a bite block. Swedish Patent No. 142,956 discloses a combined saliva evacuator and tongue positioner having a suction tube and tongue plate which are positioned by a movable chin rest and a movable jaw rest. U.S. Pat. No. 637,970 discloses a dental saliva ejector and tongue depressor having a hooked saliva evacuation tube with a deflector plate.

As can be seen, therefore, a variety of mouth props, tongue positioners and saliva evacuators for dental and oral surgery applications are known. Conventional devices, however, have some serious drawbacks. For example, conventional devices generally do not permit mouth positioning, adjustable tongue retraction, and saliva evacuation functions at the same time. Thus, an assistant is required during dental procedures to aid in performing one or more of these functions, thereby increasing the cost and time required for the dental treatment. Further, more than one instrument is generally required to carry out each of these functions simultaneously, and the multiple instruments reduce space and visibility within the patients mouth and generally increase patient discomfort.

Accordingly, there is a need for a mouth prop and tongue retractor apparatus which provides for simultaneous adjustable tongue retraction or positioning, saliva evacuation, and mouth propping functions by a single instrument, which performs these functions without requiring an assistant, which improves patient comfort and reduces time required for dental procedures, and which optimizes the space and visibility within a patient's mouth during dental procedures. The present invention satisfies these needs, as well as others, and generally overcomes the deficiencies found in the background art.

The foregoing patents reflect the state of the art of which the applicant is aware and are tendered with the view toward discharging applicant's acknowledged duty of candor in disclosing information which may be pertinent in the examination of this application. It is respectfully stipulated, however, that none of these patents teach or render obvious, singly or when considered in combination, applicant's claimed invention.

SUMMARY OF THE INVENTION

The present invention pertains to a mouth prop and tongue retraction apparatus which simultaneously provides for holding a patient's mouth in open position, adjustable retraction of a patient's tongue, and evacuation of saliva from a patient's mouth. The invention further provides for these functions to be carried out by a single instrument, without requiring the aid of an assistant.

In general terms, the invention comprises a rotating handle, a base in which the handle is rotatably mounted, a mouth prop for holding the base, tongue retraction means for positioning a patient's tongue, suction means for removing saliva from a patient's mouth, gimbal adjustment means for adjustably positioning the tongue retraction means and suction means relative to the mouth prop, and extension adjustment means for positioning of the tongue retraction means and suction means relative to the handle and base.

By way of example and not of limitation, the tongue retractor means preferably comprises a generally spatulate-shaped tongue positioner or retractor. The suction means preferably comprises an aspiration tube which is coupled to the tongue retractor means, and a suction orifice on the tongue retractor means which communicates with the aspiration tube. The handle includes an elongated axial bore which accommodates the elongated tube. The gimbal adjustment means preferably comprises a ball joint or member on the base which engages a corresponding socket joint in the mouth prop. A bore in the ball joint, which is generally co-linear with the bore in the handle, accommodates the aspiration tube. The extension adjustment means preferably comprises a threaded axial bore in the rotatable handle which accommodates a threaded portion of the elongated tube. The extension adjustment means also preferably comprises alignment means for aligning the aspiration tube relative to the base and preventing undesired rotation of the aspiration tube relative to the base and handle. The suction orifice on the tongue retractor means may optionally be included on a detachable plate which couples to the tongue retractor means.

The present invention is operated by placing the mouth prop portion of the invention between a patient's teeth or jaws in a desired position, and then having the patient bite down on the mouth prop, holding the ball joint of the base in a desired position within the socket in the mouth prop. Since the elongated tube is contained within the bore in the ball joint, rotational positioning of the ball joint relative to the socket in the mouth prop correspondingly positions the elongated tube and the attached tongue retractor. Loosening the bite on the mouth prop allows repositioning. One end of the elongated tube passes through the rotatable handle and is attached to a vacuum source to provide suction to the suction orifice, which is generally positioned under the patient's tongue. The extension adjustment of the tongue retractor is achieved by rotating the handle member so that the internal threaded portion of the handle bore drives the threaded portion of the elongated tube, causing the tube and attached tongue retractor to move. The combined gimbal adjustment means and extension adjustment means provides a greater degree of positional adjustment to the tongue retractor than is possible in currently available tongue retracting and positioning devices.

An object of the present invention is to provide a mouth prop and tongue retractor apparatus which allows simultaneous mouth positioning, tongue retraction, and saliva evacuation without requiring the assistance of additional persons.

Another object of the present invention is to provide a mouth prop and tongue retractor apparatus which allows simultaneous mouth positioning, tongue retraction, and saliva evacuation with a single instrument.

Another object of the present invention is to provide a mouth prop and tongue retractor apparatus which allows facile and accurate positioning of the tongue of a patient.

Another object of the present invention is to provide a mouth prop and tongue retractor apparatus which facilitates dental procedures by increasing the work space available in a patient's mouth.

Another object of the present invention is to provide a mouth prop and tongue retractor apparatus which facilitates dental procedures by improving visibility within a patient's mouth.

Another object of the present invention is to provide a mouth prop and tongue retractor apparatus which minimizes patient discomfort.

Another object of the present invention is to provide a mouth prop and tongue retractor apparatus which reduces time and cost associated with dental procedures.

Further objects and advantages of the present invention will be brought out in the following portions of the specification, wherein the detailed description is for the purpose of fully disclosing the invention without placing limits thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Referring more specifically to the drawings, for illustrative purposes the present invention is embodied in the apparatus generally shown in FIG. 1 through FIG. 10. It will be appreciated that the invention may vary as to configuration and as to details of the parts without departing from the basic concepts as disclosed herein.

Referring first to FIG. 1 through FIG. 5, a mouth prop and tongue retractor apparatus 10 in accordance with the present invention is generally shown. The apparatus comprises a handle 12, which is rotatably mounted in a base 14, a mouth prop 16 which holds the apparatus 10 in a patient's mouth, tongue retractor means, preferably comprising a spatulate tongue positioner or retractor 18, and suction means, preferably comprising an elongated aspiration or suction tube 20, with tube 20 communicating with a suction aperture 22 on tongue retractor 18.

Base 14 generally includes a shell portion 24 which partially encloses or houses handle 12, and a ball joint 26 which is connected to shell portion 24 by a generally cylindrical keyway alignment member 28. An axial bore 30 (FIG. 3) extends through ball joint 26 and alignment member 28, with bore 30 structured and configured to accommodate aspiration tube 20. End portion 32 of base 14 also includes an aperture 34 (FIG. 3) which receives aspiration tube 20.

Handle 12, which is preferably symmetrical in shape, is rotatably coupled to the shell portion 24 of base 14. Handle 12 includes an axial bore 36 (FIG. 3–FIG. 5) which accommodates aspiration tube 20. Handle 12 also preferably includes traction means for facilitating rotation of the handle, the traction means preferably comprising ridge 38 which extends around the circumference of handle 12. A circumferential channel 40 in shell portion 24 of base 14 accommodates ridge 38. Ridge 38 may include a plurality of serralions, grooves, or like friction generating means (not shown).

Figure 7:
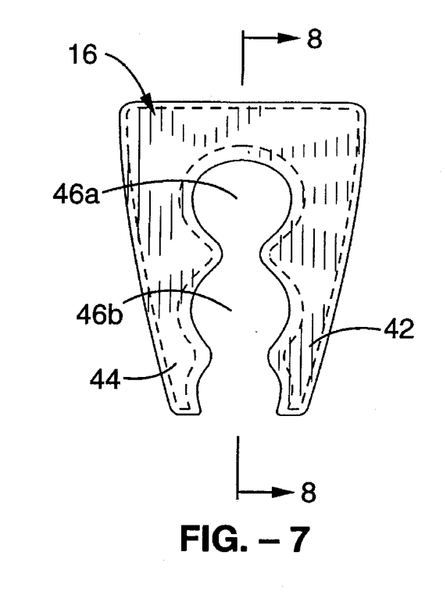
FIG. 7 is a detail plan view of the mouth prop portion of the present invention.
Figure 8:
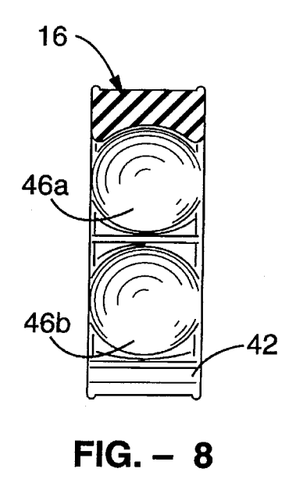
FIG. 8 is a cross-sectional view of the mouth prop of FIG. 7 taken through line 8—8.

Referring also to FIG. 7 and FIG. 8 as well as FIG. 1 through FIG. 5, mouth prop 16 generally includes upper and lower jaw- or teeth- receiving members 42, 44, which define sockets 46a, 46b which accommodate ball joint 26 on base. Mouth prop 16 is shown generally as including two sockets 46a, 46b, but may also be structured to contain only a single socket. The presence of two sockets 46a, 46b allows lateral positioning of the apparatus 10 relative to a patient's mouth, as ball joint 26 may be interchangeably fitted into either socket 46a or 46b. For reasons of clarity, ball socket 26 is generally shown as engaged in socket 46a. Mouth prop 16 is preferably fabricated from a resilient polymeric material such as ninety-durometer urethane or other similar man made or synthetic polymeric material commonly used in the dental profession, which is rigid and yet yielding enough so that it can comfortably be grasped between a patient's teeth for periods of time necessary for dental procedures. The preferred material will result in resilient upper and lower teeth receiving members 42, 44 which allow ball joint 26 to be engaged in and retained by socket 46a or 46b. A range of pivotal adjustment is possible for the apparatus 10 as discussed below, when ball joint 26 is moved within socket 46a or 46b.

Figure 3:
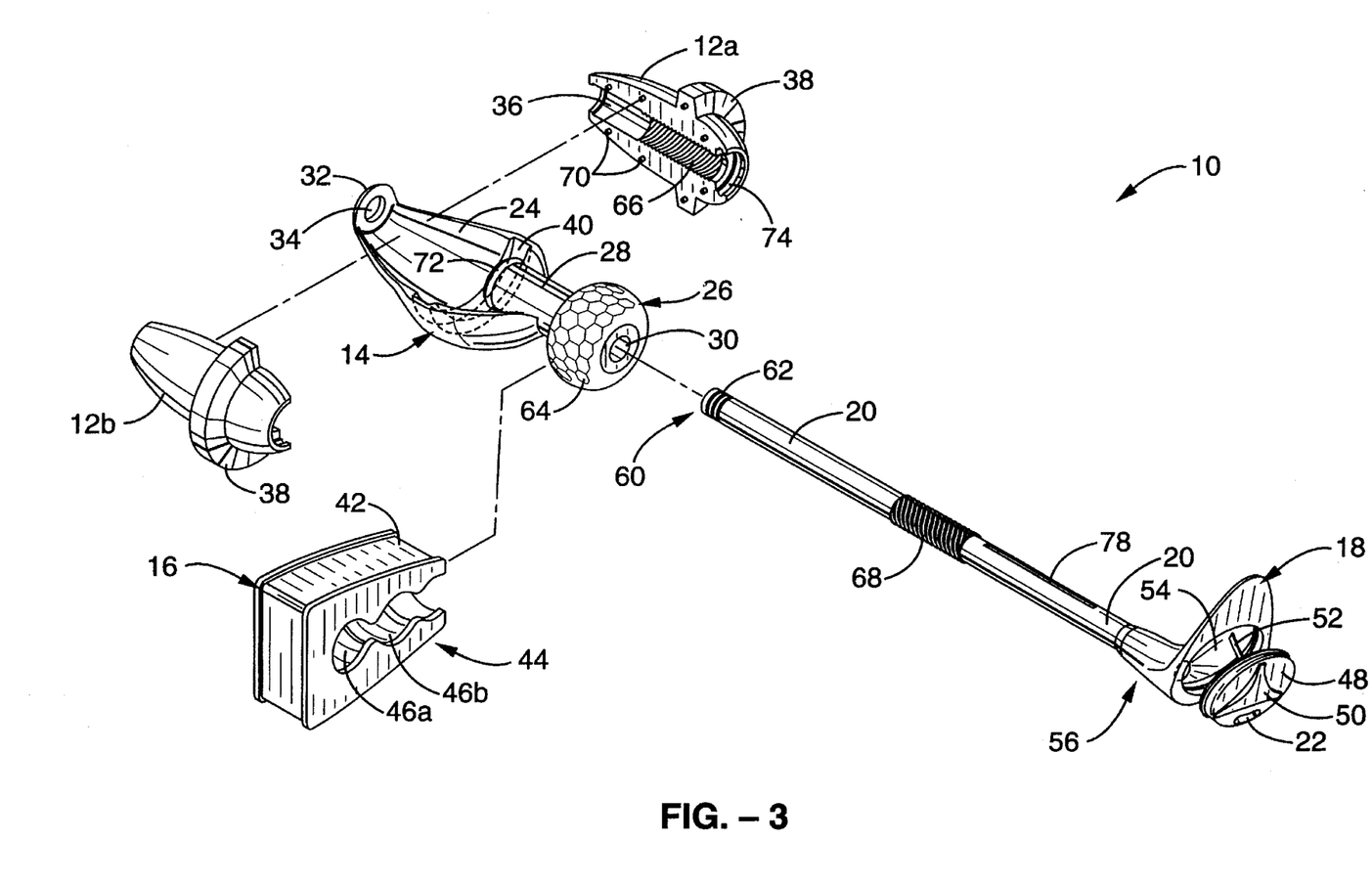
FIG. 3 is an exploded view of the mouth prop and tongue retractor apparatus shown in FIG. 1.
Figure 9:
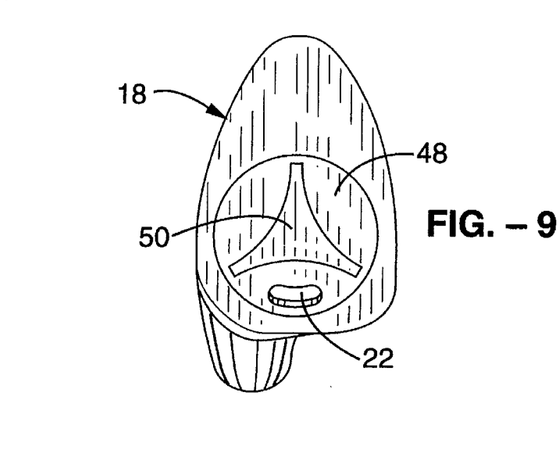
FIG. 9 is an end view of the tongue retractor portion of the apparatus shown in FIG. 1.
Figure 10:
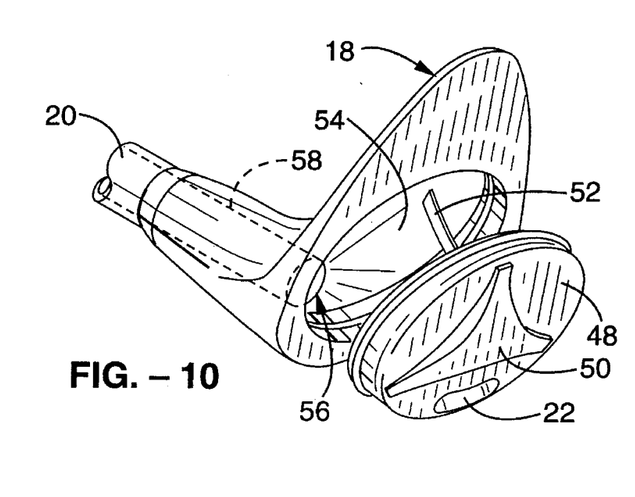
FIG. 10 is a partial perspective view of the tongue retractor shown in FIG. 9, with the tongue retractor plate exploded from the tongue retractor.

Referring also to FIG. 9 and FIG. 10 as well as to FIG. 1 through FIG. 5, tongue retractor 18 preferably includes a detachable plate 48. Plate 48 includes suction aperture 22 and gripping means for accommodating a persons fingers, shown as a generally triangular-shaped finger grip 50. Referring more particularly to FIG. 3 and FIG. 10, retention means for retaining plate 48 on tongue retractor 18 is shown as flexible tether member 52. Detachable plate 48 allows cleaning of the interior portion 54 of tongue retractor 18, while tether member 52 prevents loss of plate 48 during cleaning or sterilization of the apparatus 10. It will be appreciated, however, that plate 48 could be integrally formed as part of tongue retractor 18 instead of being removable.

Tongue retractor 18 is coupled to a first end 56 of aspiration tube 20. Aspiration tube 20 includes an axial bore 58 which is in flow communication with the interior 54 of tongue retractor 18 and suction aperture 22. Aspiration tube 20 also preferably includes frictional engagement means for attachment to a vacuum source, shown generally as a plurality of lateral ridges 62 adjacent second end 60 of aspiration tube. Tongue retractor 18 and aspiration tube 20 may be fabricated as an integral part, or may be separate parts which are joined together by standard means.

Figure 5:
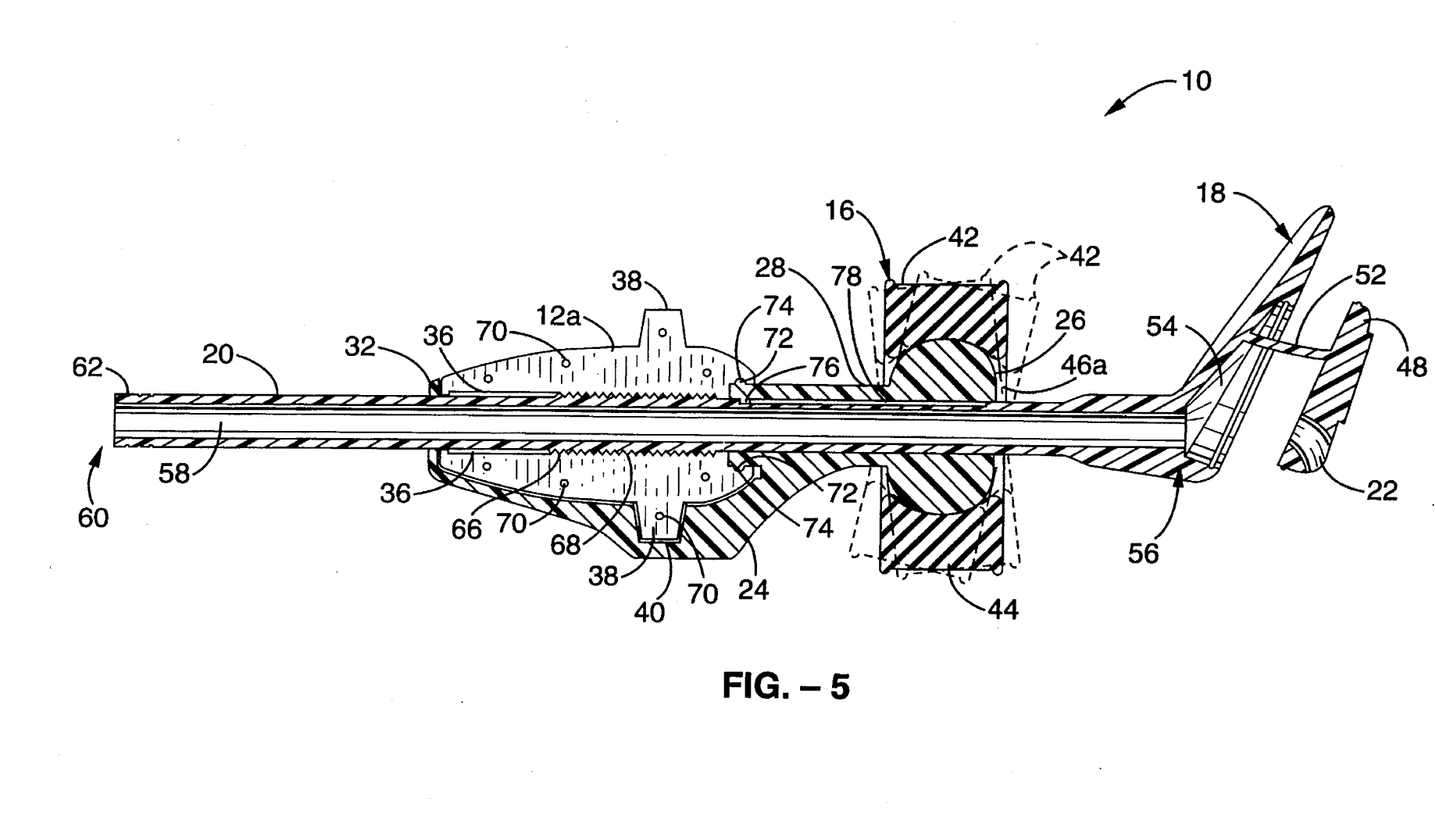
FIG. 5 is a diagrammatic view in cross-section of the mouth prop and tongue retractor apparatus shown in FIG. 4 showing the range of pivotal adjustment in the ball and socket joint as well as showing the tongue retractor plate tethered to the tongue retractor.
Figure 6:
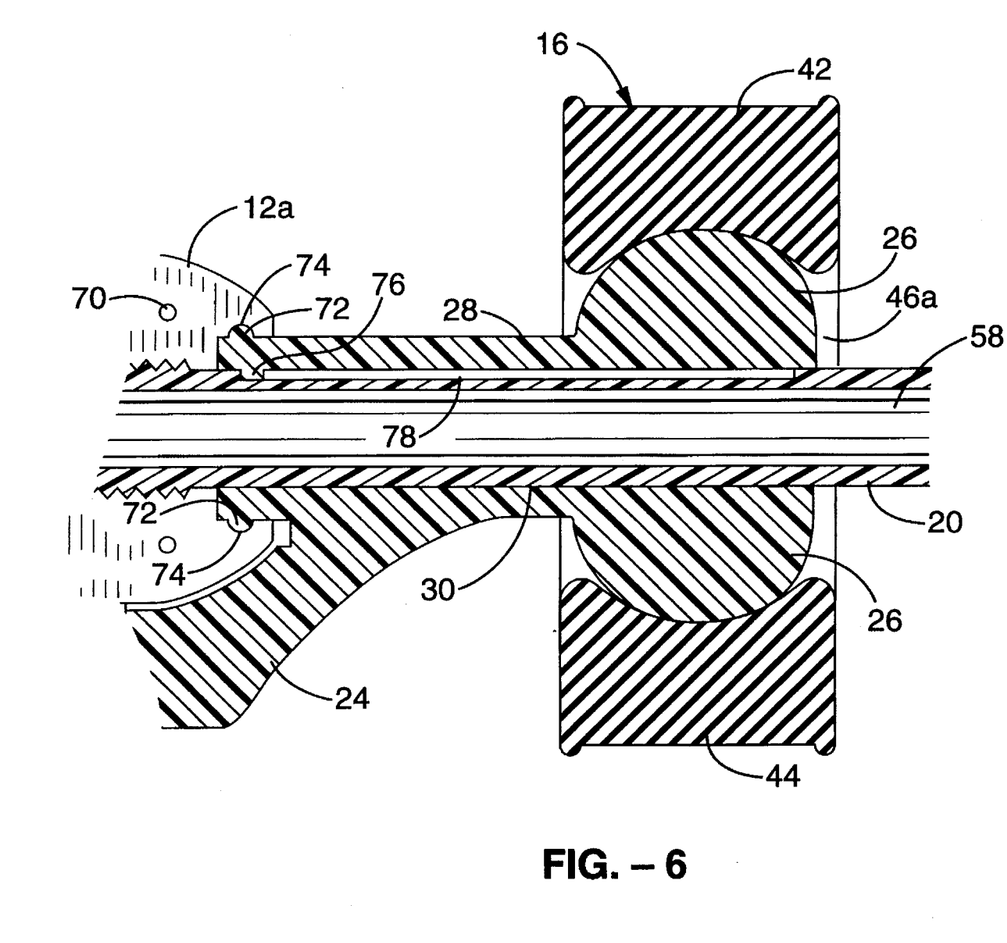
FIG. 6 is a partial sectional view of the mouth prop and tongue retractor apparatus of FIG. 1 showing the detail of the alignment keyway portion of the apparatus.

Gimbal adjustment means for positioning the tongue retractor means and suction means of the present invention are provided by the ball joint 26 of base 14, which reversibly engages socket 46a or 46b of mouth prop 16. Referring particularly to FIG. 5, tongue retractor 18 and aspiration tube 20 may be pivotally adjusted relative to mouth prop 16 as ball joint 26 pivots or swivels in socket 46a or 46b of mouth prop. Traction means, such as serrations or a grid pattern 64, may be included on ball joint to aid in holding the apparatus 10 in a particular position.

Figure 4:
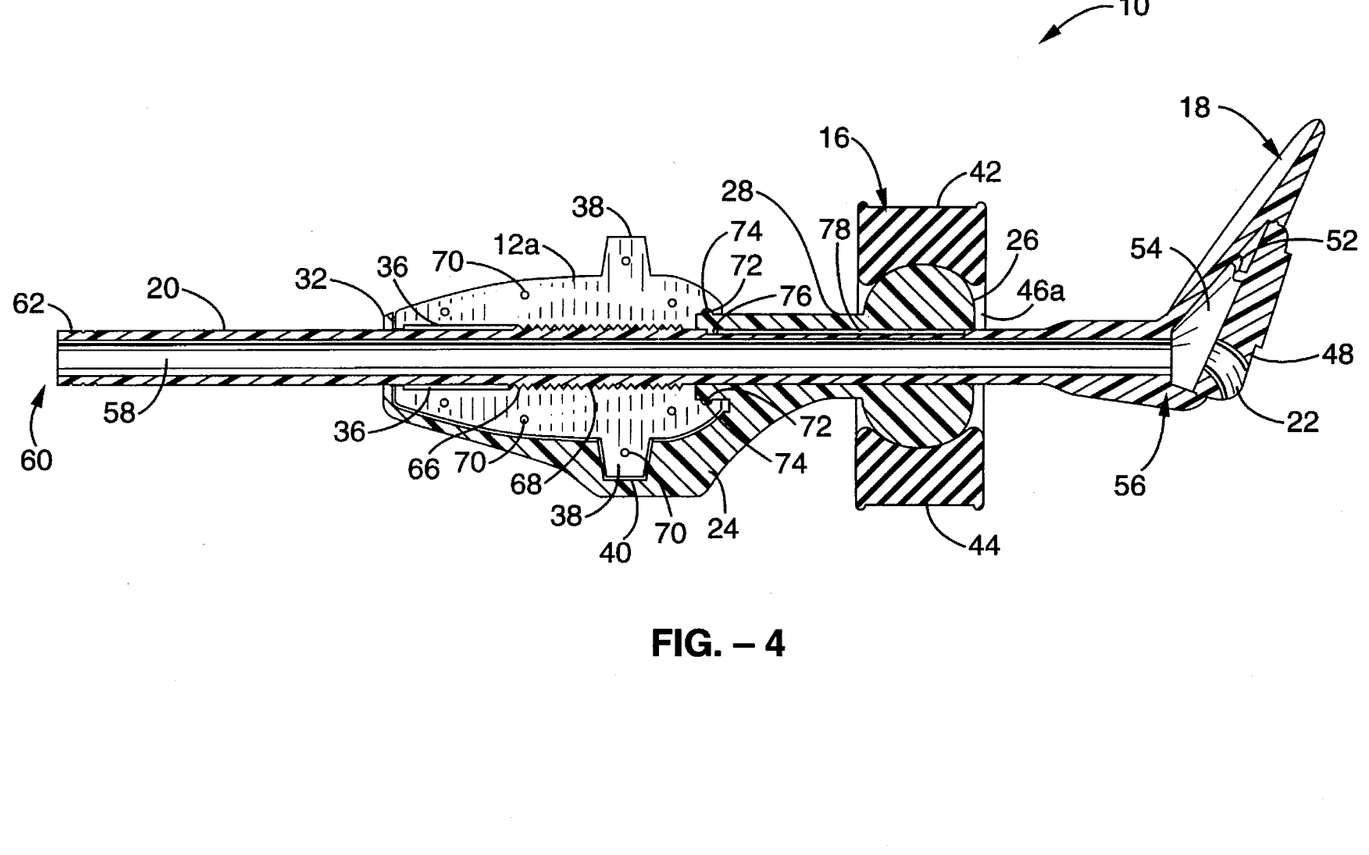
FIG. 4 is a cross-sectional view of the mouth prop and tongue retractor apparatus of FIG. 1 taken through line 4—4.

Extension adjustment means for positionally adjusting the tongue retractor means and suction means are also provided with the invention. Referring more particularly to FIG. 3, FIG. 4, and FIG. 5, the extension adjustment means preferably comprises an internal threaded portion 66 in axial bore 36 of handle 12, and an external threaded portion 68 on aspirator tube 20. Threaded portions 66 and 68 are structured and configured to reversibly engage each other. Rotational actuation of handle 12 turns threaded portion 66, which in turn drives the threaded portion 68 on aspirator tube 20, thereby extending or retracting aspirator tube 20 and tongue retractor 18 in an axial direction relative to handle 12 and base 14. The extension adjustment means may also comprise reversible application of tension on aspirator tube 20 by tension generating means associated with handle 12, so that aspirator tube may be positioned axially, and then held in place by application of tension. Such tension generating means may comprise clips, clamps, or screws (not shown) which may be internal or external to handle 12 or base 14.

Handle 12 is preferably provided in two parts or halves 12a, 12b (FIG. 3), to facilitate fitting aspirator tube 20 into bore 36 and the engagement of threaded portions 66, 68, as well as to facilitate the autoclaving, sterilizing, or cleaning generally of apparatus 10. Halves 12a, 12b are preferably held together by a stud and bore arrangement wherein a plurality of studs 70 in half 12a reversibly engage a plurality of matching bores (not shown) in half 12b by snap fitting. Retention means for retaining handle 12 in base 14 are also preferably included with the invention. As shown in FIG.3 through FIG. 6, this retention means preferably comprises a lateral ridge 72 on base 14 adjacent to keyway alignment member 28. Lateral ridge 72 engages a corresponding internal lateral groove 74 in handle 12. Lateral ridge 72 aids in retaining handle 12 within base 14 during rotational motion of handle 12.

The extension adjustment means of the present invention preferably further comprises alignment means for aligning the tongue retractor means and suction means relative to base 14 and handle 12, and for preventing rotation of the suction means and tongue retractor means relative to base 14 and handle 12. Referring particularly to FIG. 3 through FIG. 6, in the preferred embodiment the alignment means comprises an axial key 76 within axial bore 30 in keyway alignment member 28, and an axial slot or groove 78 in aspirator tube 20. Axial key 76 engages axial slot 78 such that, when handle 12 is rotated to extend or retract aspirator tube 20 as described above, aspirator tube 20 is prevented from undergoing unwanted rotational motion which would otherwise be imparted to aspirator tube 20 by the interacting threaded portions 66, 68. Alternatively, an axial key may be included on aspirator tube 20, and an axial slot included within bore 30 in keyway alignment member 28.

By way of example, the present invention is generally assembled by engaging aspirator tube 20 in bore 30 of the ball joint 26 and keyway alignment member 28 in bore 34 of base end 32 and in bore 36 of handle 12. As shown in FIG. 3, handle member 12 may be fabricated as first and second portions 12a, 12b as discussed above, which facilitates mounting of aspirator tube 20 within bore 36. Alignment key 76 is slidably engaged in alignment slot 78, and threaded portions 66, 68 of handle 12 and aspiration tube 20 are engaged with each other. Ball joint 26 is fitted into socket 46a or 46b between upper and lower teeth-receiving members 42, 44 of mouth prop 16.

Figure 1:
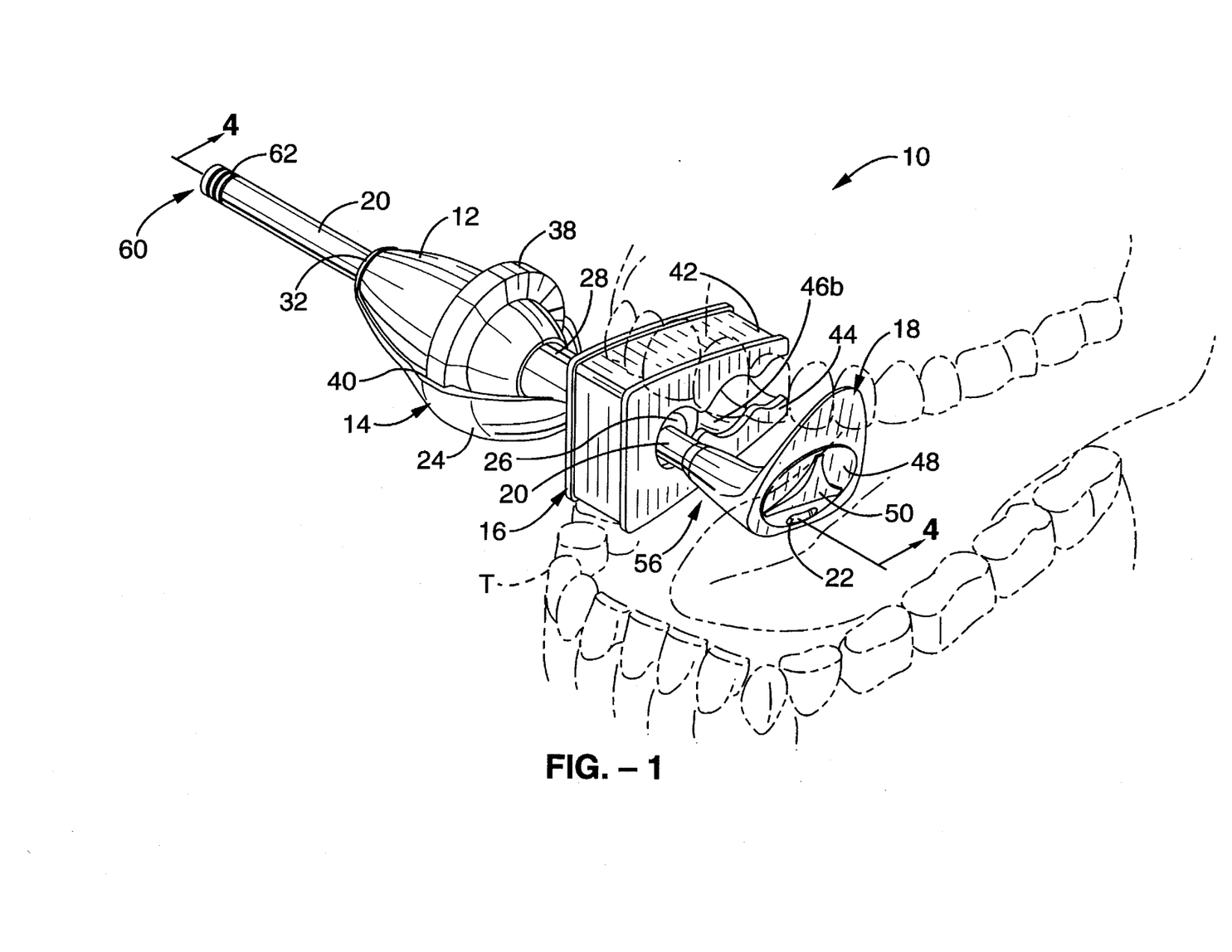
FIG. 1 is a perspective view of a mouth prop and tongue retractor apparatus in accordance with the present invention deployed in a patient's dental cavity which is shown in phantom.
Figure 2:
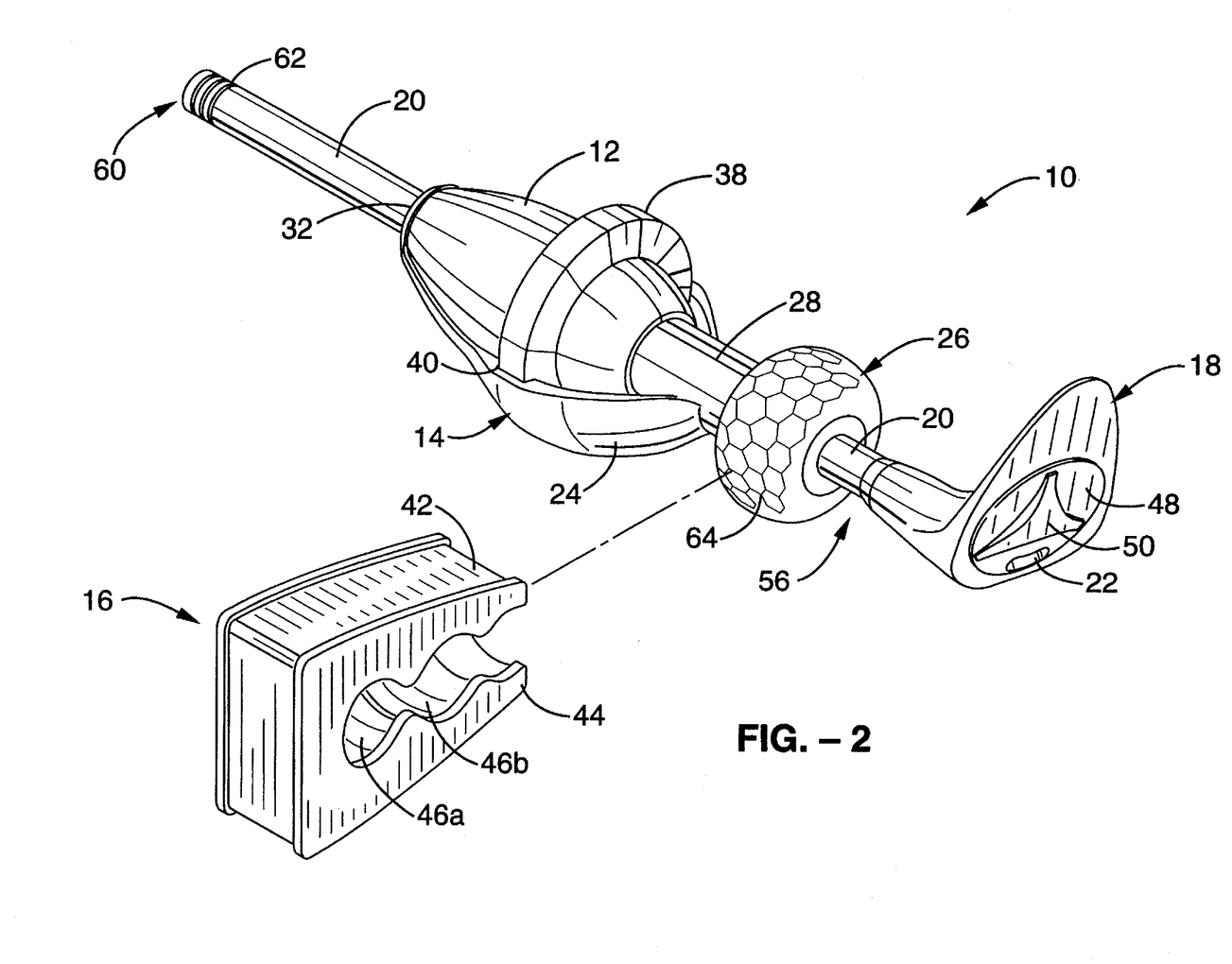
FIG. 2 is a perspective view of the mouth prop and tongue retractor apparatus of FIG. 1 shown with the mouth prop portion exploded from the ball joint portion.

The assembled apparatus 10 is used in dental and oral surgery procedures by having a patient place mouth prop 16 between the patient's teeth T, as shown in FIG. 1, with upper and lower teeth-receiving members 42, 44 positioned adjacent opposing teeth. Teeth T grasp mouth prop 16 by upper and lower teeth-receiving members 42, 44, and biting down by a patient upon upper and lower teeth-receiving members 42, 44 provides pressure on ball joint 26 within socket 46a, restricting or preventing pivotal motion of ball joint 16 within socket 22. Thus, a dentist may positionally adjust the apparatus in a desired position using the gimbal adjustment means of the invention, and then instruct a patient to apply pressure on mouth prop 16 upper and lower teeth-receiving members 42, 44 in order to retain the desired position. Similarly, a patient may instructed to relax his or her jaws to allow repositioning of the apparatus 10 by pivoting ball joint 26 within socket 46a or 46b. Extension adjustments may be made to position a patient's tongue, as shown in FIG. 1, by rotational actuation of handle 12, which engages threaded portions 66, 68 on handle 12 and aspirator tube 20, extending or retracting aspirator tube 20 and the attached tongue retractor 18 relative to handle 12 and base 14, thereby allowing precise positioning of the patient's tongue by a dentist. Saliva and materials resulting from the dental operation are evacuated from a patient's mouth through suction aperture 22 into interior 54 of tongue retractor 18 and through bore 50 in aspirator tube 20 to a vacuum hose and vacuum trap (not shown).

Accordingly, it will be seen that the present invention provides a mouth prop and tongue retractor apparatus which allows simultaneous mouth positioning, facile and accurate tongue positioning, and saliva evacuation without requiring assistance of additional persons or instruments, which increases visibility and available working space within a patients mouth, and which reduces the cost and time required for dental and oral surgery procedures. Although the description above includes many specificities, these should not be construed as limiting the scope of the invention but as merely providing illustrations of some of the presently preferred embodiments of this invention. Thus, the scope of the invention should be by the appended claims and their legal equivalents.

What is claimed is:

1. A mouth prop and tongue retractor apparatus, comprising:
   (a) a handle;
   (b) a base, said handle rotatably coupled to said base;
   (c) a mouth prop, said mouth prop coupled to said base;
   (d) tongue retractor means for positioning a patient's tongue;
   (e) suction means for removing saliva front a patient's mouth, said suction means coupled to said tongue retractor means;
   (f) gimbal adjustment means for adjustably positioning said tongue retractor means and said suction means relative to said mouth prop; and
   (g) extension adjustment means for positioning said tongue retractor means and said suction means relative to said handle and said base.

2. An apparatus as recited in claim 1, wherein said suction means comprises an aspiration tube, said aspiration tube coupled to said tongue retractor means, said suction means further comprising a suction aperture on said tongue retractor means, said aspiration tube in flow communication with said suction aperture.

3. An apparatus as recited in claim 2, wherein said handle includes a bore and wherein said ball joint includes a bore, said bore in said handle positioned collinear with said bore in said ball joint, said aspiration tube extending through said bore in said handle and said bore in said ball joint.

4. A mouth prop and tongue retractor apparatus as recited in claim 3, wherein said extension adjustment means comprises an internal threaded portion in said bore in said handle and an external threaded portion on said aspiration tube, said threaded portion in said bore in said handle engaging said threaded portion on said aspiration tube.

5. A mouth prop and tongue retractor apparatus as recited in claim 4, wherein said extension adjustment means further comprises means for aligning said aspiration tube relative to said base and said handle and preventing rotation of said aspiration tube relative to said base AND said handle.

6. A mouth prop and tongue retractor apparatus as recited in claim 2, wherein said tongue retractor means further comprises a detachable plate, said suction aperture included on said detachable plate.

7. A mouth prop and tongue retractor apparatus as recited in claim 6, wherein said tongue retractor means further comprises retention means for retaining said plate when detached from said tongue retractor.

8. An apparatus as recited in claim 1, wherein said gimbal adjustment means comprises a ball joint included on said base and a socket included in said mouth prop, said ball joint pivotally coupled to said socket.

9. A mouth prop and tongue retractor apparatus, comprising:
   (a) a handle, said handle including an axial bore;
   (b) a base, said base including a ball joint, said ball joint including an axial bore, said handle rotatably coupled to said base;
   (c) a mouth prop, said mouth prop including a socket, said ball joint pivotally coupled to said socket;
   (d) an aspiration tube, said aspiration tube extending through said axial bore in said handle and said axial bore in said ball joint;
   (e) a tongue retractor, said tongue retractor including at least one suction aperture, said tongue retractor coupled to said aspiration tube; and
   (f) extension adjustment means for positioning said tongue retractor relative to said handle and said base by rotation of said handle relative to said base.

10. An apparatus as recited in claim 9, wherein said extension adjustment means comprises an internal threaded portion in said bore in said handle and an external threaded portion on said aspiration tube, said threaded portion in said axial bore in said handle engaging said threaded portion on said aspiration tube.

11. An apparatus as recited in claim 10, wherein said extension adjustment means further comprises alignment means for aligning said aspiration tube relative to said base and preventing rotation of said aspiration tube relative to said base.

12. An apparatus as recited in claim 11, wherein said alignment means comprises a keyway alignment member, said keyway alignment member positioned on said base, said keyway alignment member including an axial bore, said bore in said keyway alignment member being collinear with said bore in said ball joint and said bore in said handle, said aspiration tube mounted within said bore in said keyway alignment member, said bore in said keyway alignment member including an axial groove, said aspiration tube including an axial key, said key on said aspiration tube slidably engaging said groove in said bore in said keyway alignment member.

13. An apparatus as recited in claim 9, wherein said tongue retractor means further comprises a detachable plate, said suction aperture positioned on said detachable plate, said suction aperture positioned in flow communication with said aspiration tube, said tongue retractor including retention means for retaining said detachable plate.

14. A mouth prop and tongue retractor apparatus, comprising:
   (a) a handle, said handle including an axial bore, said bore including a threaded portion;
   (b) a base, said base including a ball joint, said ball joint having an axial bore, said handle rotatably coupled to said base, said bore in said ball joint positioned collinear with said bore in said handle;
   (c) a mouth prop, said mouth prop including an upper teeth receiving member, said mouth prop including a lower teeth receiving member, said upper and lower teeth receiving members defining a socket, said ball joint pivotally coupled to said socket;

(d) an elongated aspiration tube, said aspiration tube extending through said bore in said handle and said bore in said ball joint, said tube including an external threaded portion, said threaded portion of said tube reversibly engaging said threaded portion of said bore in said handle;

(e) a tongue retractor, said tongue retractor coupled to said aspiration tube, said tongue retractor including a detachable plate, said detachable plate including suction aperture, said suction aperture in flow communication with said aspiration tube; and (f) alignment means for aligning said aspiration tube relative to said base and preventing rotation of said aspiration tube relative to said base.

15. An apparatus as recited in claim 14, wherein said base includes a shell portion, said shell portion of said base partially enclosing said handle.

16. An apparatus as recited in claim 15, wherein said alignment means comprises a keyway alignment member, said keyway alignment member positioned on said base, said keyway alignment member connecting said ball joint and said shell portion of said base, said keyway alignment member including an axial bore, said bore in said keyway alignment member positioned collinear with said bore in said ball joint and said bore in said handle, said aspiration tube extending through said bore in said keyway alignment member.

17. An apparatus as recited in claim 16, wherein said alignment means further comprises an axial key, said key positioned within said axial bore of said keyway alignment member, said alignment means further comprising an axial groove on said aspiration tube, said axial key slidably engaging said axial groove in said aspiration tube.

18. An apparatus as recited in claim 14, wherein said aspiration tube includes a first end and a second end, said tongue retractor coupled to said first end of said aspiration tube, said second end of said tube including means for attachment to a vacuum source.

19. An apparatus as recited in claim 14, wherein said tongue retractor further comprises retention means for retaining said detachable plate.

20. An apparatus as recited in claim 14, wherein said ball joint further comprises traction means for generating friction with said socket in said mouth prop.

* * * * *